United States Patent
Boudjema et al.

(10) Patent No.: US 11,660,117 B2
(45) Date of Patent: May 30, 2023

(54) IMPLANTATION DEVICE WITH DIRECT-TO-NEEDLE ASPIRATION OF HAIR GRAFT

(71) Applicant: Boudjema-Rassman Partnership, Corona Del Mar, CA (US)

(72) Inventors: Pascal Boudjema, Paris (FR); William R Rassman, Los Angeles, CA (US)

(*) Notice: Subject to any disclaimer, the term of this patent is extended or adjusted under 35 U.S.C. 154(b) by 0 days.

(21) Appl. No.: 17/398,344

(22) Filed: Aug. 10, 2021

(65) Prior Publication Data

US 2023/0048841 A1 Feb. 16, 2023

(51) Int. Cl.
*A61B 17/34* (2006.01)
*A61F 2/10* (2006.01)
*A61B 17/00* (2006.01)

(52) U.S. Cl.
CPC ............ *A61B 17/3468* (2013.01); *A61F 2/10* (2013.01); *A61B 2017/00561* (2013.01)

(58) Field of Classification Search
CPC .............................. A61F 2/10; A61B 17/3468
See application file for complete search history.

(56) References Cited

U.S. PATENT DOCUMENTS

| | | | |
|---|---|---|---|
| 4,126,124 A | 11/1978 | Miller | 606/187 |
| 4,160,453 A | 7/1979 | Miller | 606/187 |
| 4,874,367 A | 10/1989 | Edwards | 604/72 |
| 5,417,683 A | 5/1995 | Shiao | 606/1 |
| 5,439,475 A | 8/1995 | Bennett | 606/187 |
| 5,562,613 A | 10/1996 | Kaldany | 604/57 |
| 5,611,811 A | 3/1997 | Goldberg | 606/187 |
| 5,827,297 A | 10/1998 | Boudjema | 606/187 |
| 5,911,703 A | 6/1999 | Slate et al. | 604/68 |
| 6,059,807 A | 5/2000 | Boudjema | 606/187 |
| 7,144,406 B2 | 12/2006 | Pak et al. | 606/187 |
| 7,261,721 B2 | 8/2007 | Feller | 606/133 |
| 7,452,367 B2 | 11/2008 | Rassman et al. | 606/187 |
| 8,062,322 B2 | 11/2011 | Rassman et al. | 606/187 |
| 10,813,667 B1 | 10/2020 | Boudjema et al. | A61F 2/10 |
| 2004/0193203 A1 | 9/2004 | Pak et al. | A61B 17/34 |
| 2005/0187573 A1 | 8/2005 | Rassman et al. | A61B 17/34 |
| 2008/0009896 A1 | 1/2008 | Shiao | 606/187 |
| 2008/0051816 A1 | 2/2008 | Pak et al. | 606/187 |
| 2008/0167674 A1 | 7/2008 | Bodduluri et al. | 606/187 |
| 2014/0188150 A1 | 7/2014 | Oc et al. | 606/187 |
| 2016/0015424 A1 | 1/2016 | Kim et al. | 606/187 |
| 2016/0120574 A1 | 5/2016 | Shiao | 606/187 |

FOREIGN PATENT DOCUMENTS

| | | |
|---|---|---|
| JP | H04-152944 | 5/1992 |
| WO | 2012/136904 | 10/2012 |
| WO | 2015/186146 | 12/2015 |

OTHER PUBLICATIONS

Search Report and Written Opinion dated Nov. 1, 2022 in in counterpart PCT Application No. PCT/US2022/039613.

*Primary Examiner* — Jason-Dennis N Stewart
(74) *Attorney, Agent, or Firm* — Venable LLP

(57) ABSTRACT

Device and method for implantation of hair grafts into the scalp of a patient. In the device, a cross-sectional shape of a rod riding in an implantation needle is configured with respect to the needle to communicate a vacuum in a chamber anterior to the needle forward to an interior of the needle, thereby facilitating loading of the hair graft into the device by direct-to-needle aspiration of the hair graft.

10 Claims, 8 Drawing Sheets

IMPLANTATION DEVICE WITH DIRECT-TO-NEEDLE ASPIRATION OF HAIR GRAFT

BACKGROUND

1. Field

The field of the present disclosure is generally related to surgical implantation devices and surgical methods for implantation of hair grafts into the scalp of a patient.

2. Description of the Related Art

In preparation for implantation of hair grafts into the scalp of a patient, great care must be taken to prevent damage or injury to the living graft so as to ensure that it thrives in the implantation site. Damage has become an even greater concern as the art of hair transplantation has progressed to implantation of grafts comprised of individual follicular units, given the very small size of the follicular units and their consequent increased susceptibility to damage.

Many steps are needed to achieve a successful implantation, from harvesting and separation of hair grafts into individual follicular units, to loading of the graft into the implantation device, to actual implantation of the hair graft and subsequent withdrawal of the implantation needle from the graft site.

Especially with respect to damage that might be caused during loading of the graft into the implantation device, U.S. Pat. No. 7,144,406, "Hair transplant device", describes aspiration of the hair graft directly into the needle of the implantation device, using a vacuum introduced into the needle by a side opening in the needle. In such a device, however, the graft may become damaged by extrusion of part of the graft into the low pressure side port, such that part of the loaded graft may become stuck in the side port and damaged laterally by withdrawal of the needle during implantation.

SUMMARY

It is an object of the present disclosure to describe an implantation device that reduces the possibility of damage to the graft especially during the loading step.

According to one embodiment herein, a device for implantation of hair grafts includes a handpiece extending along a longitudinal axis, wherein the handpiece has a sheath mounted to a forward end thereof and a channel to which a source of vacuum is connectable. A piston is slidably mounted in the handpiece and is movable between a rest position and an action position, wherein the piston is biased to the rest position, wherein in the rest position the piston defines a chamber in the handpiece and forward of the piston, and wherein the handpiece has an orifice that vents the chamber to an outside of the handpiece. A hollow needle is fixed to a forward end of the piston and extends into the sheath. A central rod is fixed to the handpiece and extends into the hollow needle, wherein a cross-section of the rod is configured with respect to the needle to communicate a vacuum in the chamber to an interior of the needle. In the rear position the hollow needle is sheathed by the sheath, and closure of the orifice creates a vacuum in the chamber to move the piston to the action position where the piston extends the needle forwardly beyond the sheath such that the vacuum in the chamber is communicated via the cross-sectional shape of the rod to aspirate a hair graft into the needle.

According to certain aspects described herein, the aspirated graft is inserted by the needle into a scalp incision while the orifice is closed and the piston extends the needle forwardly beyond the sheath. Subsequent to insertion of the graft the orifice is opened causing the piston and the needle to retract to the rest position while the rod retains the graft implanted at its insertion position in the incision. The needle may comprise a sharp bevel-shaped tip configured to form the incision into a scalp for implantation of the hair graft. The needle may be mounted for rotational motion with respect to the handpiece so as to allow rotation of the bevel with respect to the orifice.

According to certain aspects described herein, the central rod is adjustably fixed to the handpiece along the longitudinal direction thereof so as to adjust an implantation depth of the hair graft.

According to certain aspects described herein, the central rod may have a circular cross-section and the gap is an annular gap around the circumference of the central rod. The central rod may have a cross-section comprised of at least one of cross-sections that are cruciform, polygonal, star-shaped and hollow, or a combination of such cross-sections.

Further objectives and advantages will become apparent from a consideration of the description, drawings, and examples.

DETAILED DESCRIPTION

First Embodiments

Figure 1:
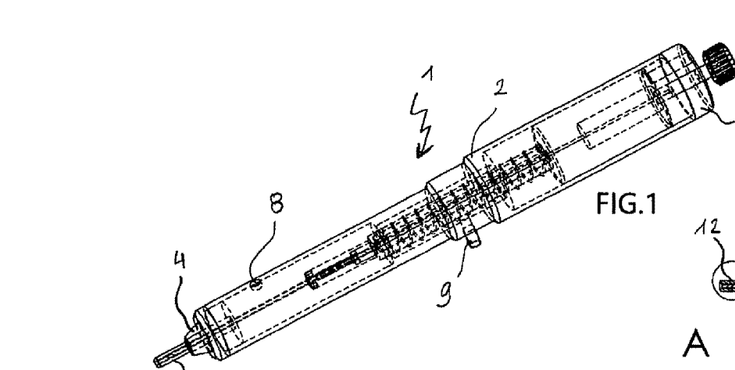
FIG. 1 is a perspective view showing a first embodiment of a device according to the description herein at rest position with the needle retracted inside the body of the instrument.
Figure 2:
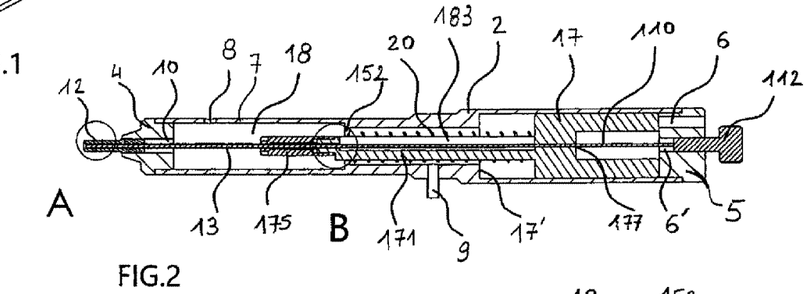
FIG. 2 is a longitudinal sectional view of the instrument of FIG. 1.
Figure 3:
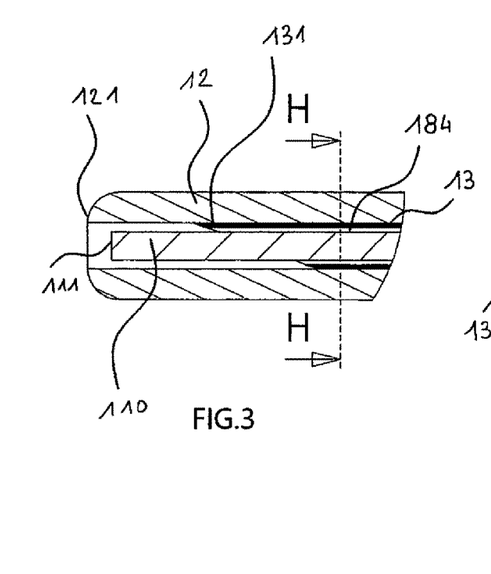
FIG. 3 is a detailed view of part A of FIG. 2.

FIGS. 1 to 3 are views of a graft implantation device 1 according to the description herein in a rest position in which an implantation needle is in the retracted position in a sheath located at the front of the instrument.

As described in FIGS. 1 to 5, the implantation device is composed of an instrument or handpiece 1 of cylindrical tubular shape 2 inside which a piston 17 is mobilized between two positions: a rest position or rear position and an anterior action position or front position. The handpiece is closed at its rear end by a plug 5 and at its front end by a cylindrical-conical plug 4. The space between the piston 17, the wall 7 of the cylinder 2 and the plug 4 defines a chamber 18. The rear plug 5 is pierced over its entire length with an eccentric air exhaust bore 6 and a threaded axial central bore 6' suitable for securely holding an adjustment screw 112 extended forward by a straight central rod 110 of cylindrical shape of very small diameter extending axially over the entire length of the hand piece 1. The piston 17 is pierced right through with a central bore 177 suitable for making the central rod 110 freely slide in a sealed manner. The piston 17 can be mobilized inside the cylinder 2 between a rear position in contact with the rear cap 5 and a front position against a stop 17'.

The piston 17 is extended forward by an extension 171 of smaller outer diameter of cylindrical shape at the end of which is arranged an axial fixing device of the type of mandrel or chuck 175 for clamping a hollow cylindrical rectilinear needle 13. The extension of the piston 171 has a space or recess 183 opened into the chamber 18 so that the central rod 110 can pass through it completely freely and without contact as will be described later. Likewise, the hollow needle 13 has over its entire length a constant internal diameter greater than the diameter of the rod 110 so that said rod can pass through it completely freely and without contact, as will be described below.

A compression return spring 20 is arranged around the extension 171 of the piston 17. The spring 20 resting on an annular fixed shoulder 152, keeps the piston 17 in the rear rest position in contact with the plug 5 when the instrument is at rest.

The handpiece 1 is pierced at its front and upper part in its wall 7 near the plug 4 by an air exhaust orifice 8 making it possible to communicate the outside ambient air with the chamber 18. The handpiece also has at its lower and middle part a rigid tube or nozzle 9 making it possible to communicate the air contained inside the chamber 8 to an external vacuum source by a flexible tubing (not shown).

The orifice 8 is intended to be blocked by the index finger of an operator's hand (not shown) in order to create an air depression inside the handpiece and to mobilize forward the piston 17 inside the chamber 18 as it will be described later in FIG. 6B.

The conical plug 4 is drilled in its center axially over its entire length with a bore 10 which is partly threaded suitable for adapting thereto a tubular sheath 12 which is partly threaded on the outside. The sheath 12 is pierced right through in its center with a bore of the same diameter as the outer diameter of the needle 13 so that said needle can slide therein in a sealed manner. The sheath 12 has a free end 121 intended to come into abutment against the skin as will be described below.

Figure 4:
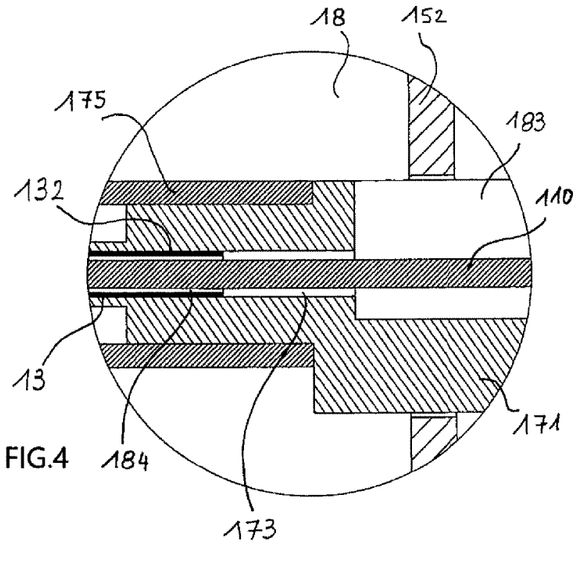
FIG. 4 is a detailed view of part B of FIG. 2.

FIGS. 3 and 4 are detail views A and B of FIG. 2 showing the positioning respectively of the anterior and posterior ends of the hollow needle 13 in the retracted position or rest position of the instrument 1.

In FIG. 3, the anterior end 131 of the bevelled-shaped needle 13 is disposed inside the sheath 12 set back from the free end 121 of said sheath. The hollow needle 13 of rectilinear and cylindrical shape, the dimensions of which can be around 1 millimeter in external diameter and 0.8 millimeter in internal diameter over 50 millimeters in length, is configured to move freely axially in contact with the sheath 12 in a hermetic manner. In this rest position, the end 131 of the needle 13 is also set back relative to the free end 111 of the central rod 110.

Figure 5:
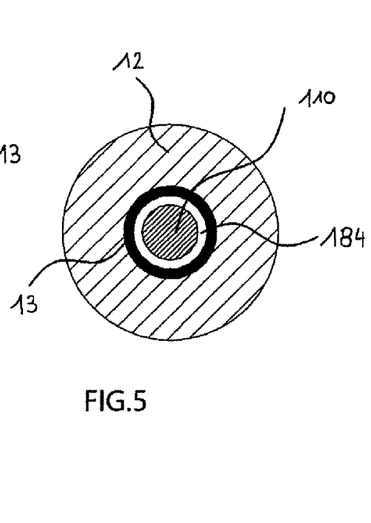
FIG. 5 is an enlarged cross-sectional view E-E of FIG. 3.

In FIG. 5 which is an enlarged sectional view along E-E of FIG. 3, we see that the rod 110 is separated from the inner wall of the needle 13 by an empty space 184 of annular shape. This empty space 184 located between the rod 110 and the needle 13 and extending over the entire length of the needle 13 allows the air contained inside the instrument to communicate freely in the chamber 18 up to at the anterior end 131 of needle 13.

As illustrated in FIG. 4, the posterior part 132 of the needle 13 is fixed tightly at its periphery to the extension 171 of the piston 17 in a central axial channel 173 by means of a clamping mandrel 175 allowing easy replacement. and quickly if necessary the needle 13 during the operation. It can be seen that the rod 110 is disposed inside the needle 13 and separated from it by the space 184 as indicated above.

FIGS. 6A, 6B, 7 and 8 are views of the implantation device according to the description herein in a action position where the piston 17 is in the front position within the instrument as well as the needle 13 protruding from the outside. outside the sheath 12.

The implantation device being connected by a flexible pipe to a continuously operating vacuum source (for example about 800 mBar of negative pressure not shown) through channel 9, the obstruction of orifice 8 by the index finger of the 'operator (not shown) will cause a sudden depression inside the chamber 18 causing within the instrument the almost instantaneous movement towards the front of the piston 17 against the stop 17' and consequently the movement towards the front of the needle 13 relative to the sheath 12 over an equivalent distance (for example about 10 millimeters).

Figures 6A, 6B, 7, 8:
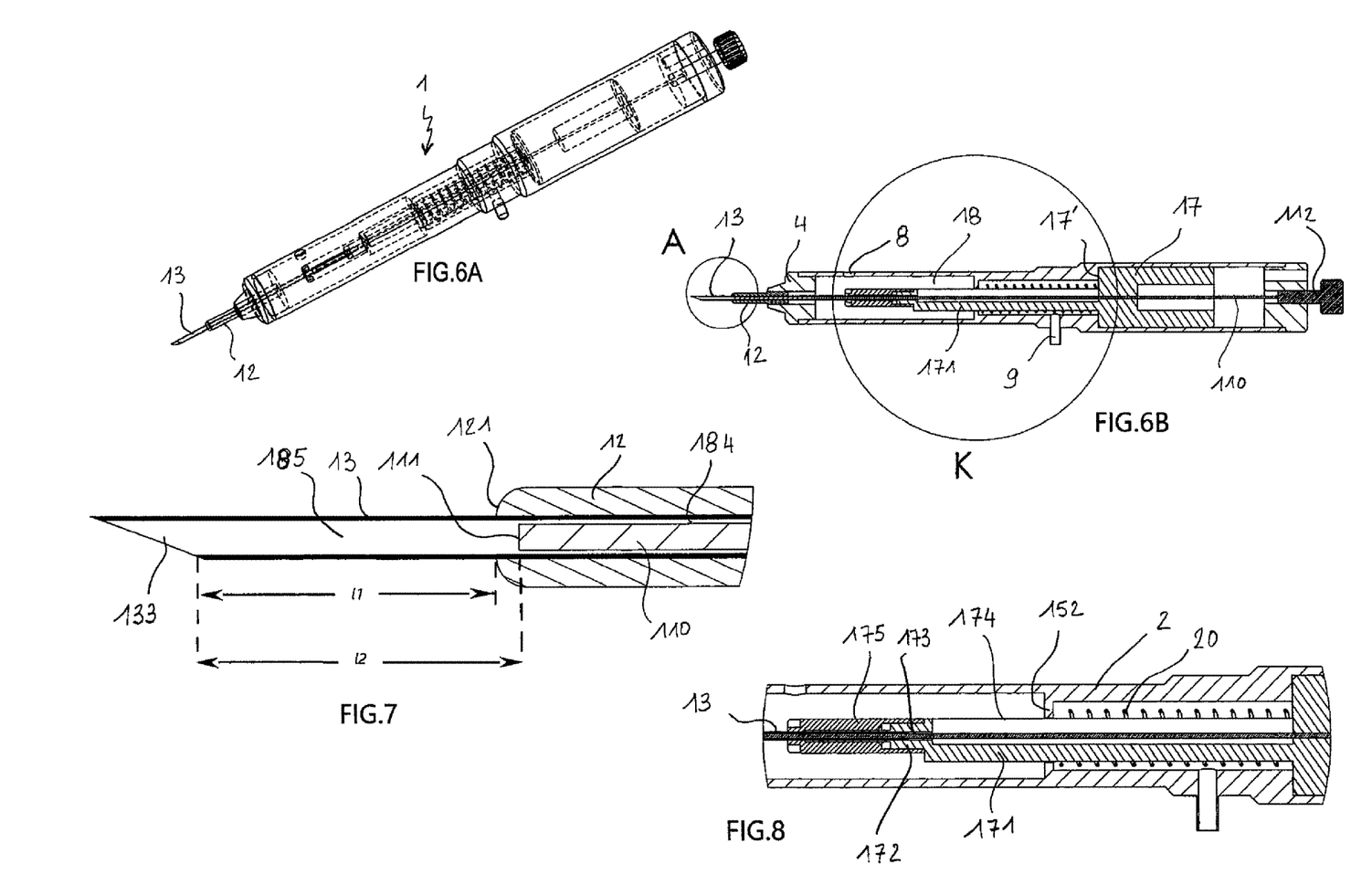
FIG. 6A is a perspective view of the device of FIG. 1 in action with the needle extending at the front part of the instrument.
FIG. 6B is a longitudinal sectional view of the instrument of FIG. 6A.
FIG. 7 is an enlarged detailed view of part A of FIG. 6B.
FIG. 8 is an enlarged detailed view of part K of FIG. 6B.

In this position of action, as illustrated in FIG. 7, the hollow needle 13 is partly exteriorized projecting at the front of the instrument 1 beyond the end 121 of the sheath 12 for a distance "l1" such that a cylindrical space 185 is created inside the needle capable of totally containing a graft (not shown) over a distance "l2" between the bevelled open end 133 of the needle 13 and the end 111 of the rod 110. It should be noted that the distance "l1" corresponds to the length of the needle which is introduced into the skin. This length "l1" is adjustable according to the variable thickness of the skin during the operation by screwing or unscrewing the sheath 12 relative to the cylindrical-conical plug 4 as illustrated above. It should also be noted that the length "l2" can be adjusted during the operation by screwing or unscrewing the adjusting screw 112 in the rear plug 5 so that the end 111 of the rod 110 can be slightly withdrawal or at the same level or even slightly forward with respect to the end 121 of the sheath 12 so that the graft is placed more or less deeply into the skin (not shown) as desired by the operator, when the withdrawal of the needle 13 inside the sheath 12.

It should be noted that in this action position, a continuous flow of external air is created in the instrument 1 by circulating respectively from the open end 133 of the needle 13 in the cylindrical space 185, in the annular space 184, in the channel 173, the space 183 and the chamber 18 up to the rigid tube 9 connected to a vacuum source (not shown). In this position of action, the needle 13 becoming "aspirating" is thus ready to suck and fully load a graft previously placed for example on a moist gauze or the back of the hand (not shown) inside the space 185 for implantation in the skin.

Medical practice has shown, for example, that the annular void space 184 between a rod 110 of approximately 0.6 millimeter in diameter and a needle 13 of approximately 0.8 millimeter in internal diameter and 50 millimeters in length, was large enough to transmit a sufficiently large suction in the space 185 such that bringing the bevelled end 133 into contact with a graft of about 0.8 to 1 millimeter in diameter (not shown) can easily suck and lodge the latter in the space 185 on contact of the end 111 of the rod 110. It is also interesting to note that the part of the graft in contact with the end 111 does not undergo any deformation or asymmetric invagination in the space 184 due to the circular, homogeneous and uniform concentric suction forces exerted on the graft. This feature thus prevents the graft from being stuck or damaged between the rod 110 and the needle 13.

FIG. 8 is an enlarged view of detail K of FIG. 6B detailing a means of preventing any axial rotation of the piston 17 with respect to the cylinder 2 of the implantation instrument according to an embodiment of the description herein. The extension 171 of the cylindrical-shaped piston has a flat or flat surface 174 at its upper part coming into contact with an annular fixed shoulder 152 disposed at the middle part of the instrument having a complementary profile opening such that the extension 171 can move in axial translation freely inside the instrument without the possibility of rotation. Locking the piston from rotation thus prevents axial rotation of the needle 13 so that its bevel 133 can always be positioned in the same predefined plane relative to the implantation instrument. Indeed, medical practice has shown that the graft was better stabilized in the skin when the needle 13 was introduced into the skin obliquely in relation to the skin surface with its bevel still facing the skin. This avoids the operator having to frequently rotate the instrument in order to position the bevel facing the skin, which is a waste of time. The annular fixed shoulder 152 also serves as an anterior point of support for the spring 20.

FIG. 8 also shows a first method of fixing the needle 13 to the extension 171 of the piston by a clamping mandrel 175. In fact, this type of fixing allows the rapid replacement during the intervention of the implantation needle 13 positioned in the central channel 173 by screwing and unscrewing the mandrel 175 at the threaded end 172 of the extension 171 using a suitable key (not shown).

Figures 9, 10E:
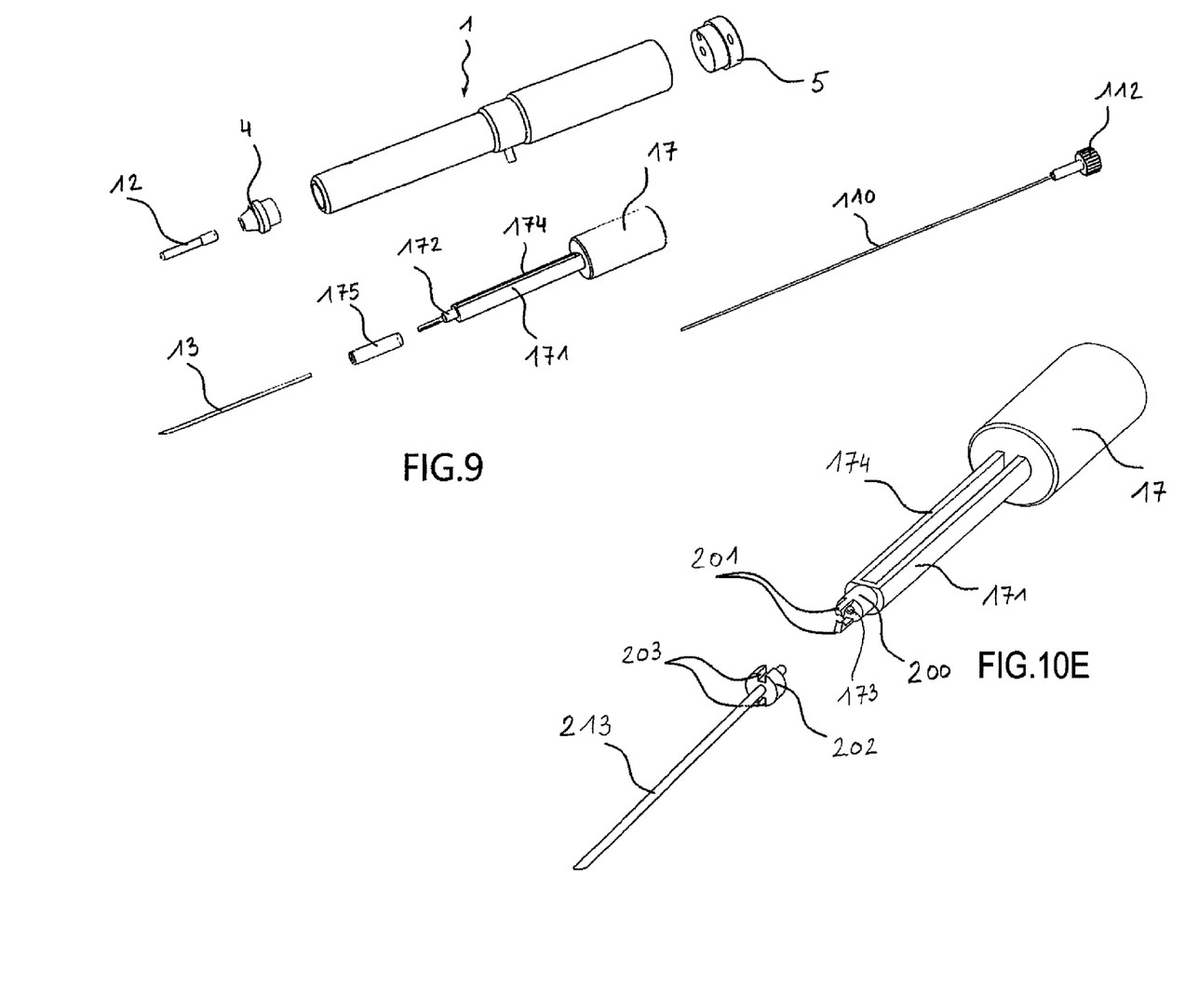
FIG. 9 is an exploded view of the instrument showing the different parts of the instrument of FIG. 1.
FIG. 10E is a perspective view showing a second alternative of fixation of the needle to the piston of a device according to the description herein.

FIG. 9 is an exploded view showing the various constituent elements of the implantation device according to an embodiment of the invention described above and more particularly the means for fixing the needle 13 to the piston 17 by means of the clamping mandrel 175 in the threaded end 172.

Figure 10A:
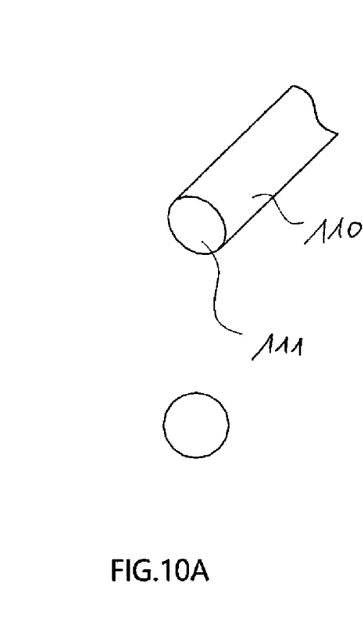
FIG. 10A to 10D are perspective and front views of different shapes of the rod of a device according to the description herein.
Figure 10B:
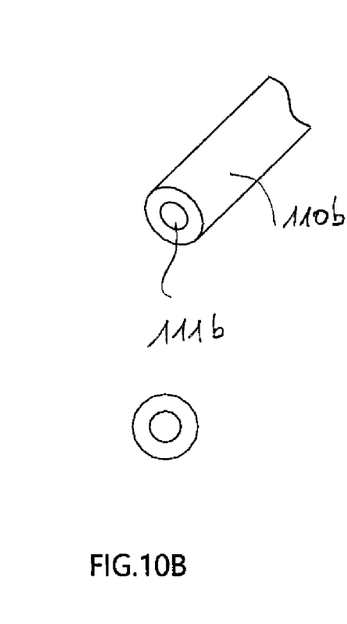
Figure 10C:
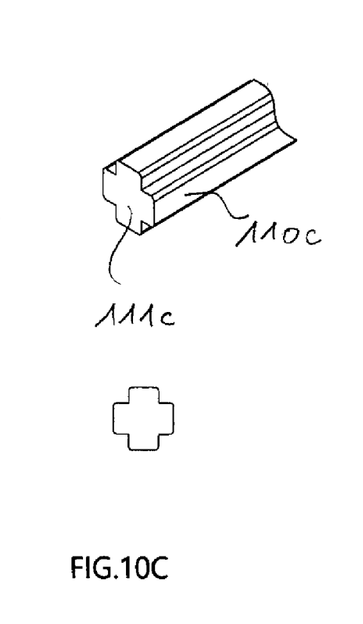
Figure 10D:
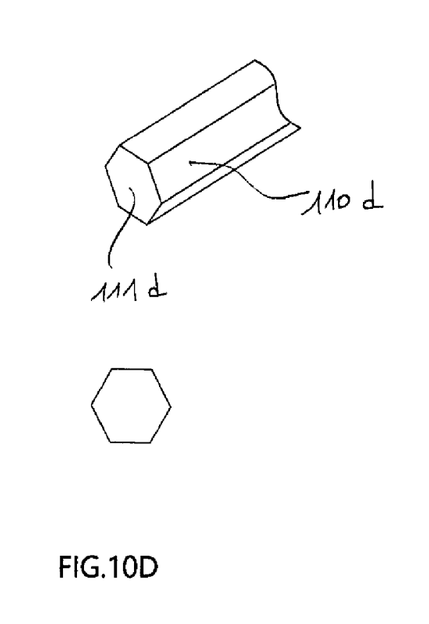

FIG. 10A shows a shape of cylindrical rod adapted inside the needle as described in FIGS. 1-9 which diameter is lesser than inside diameter of the needle for the purpose of maintaining a free space between the rod and the needle. FIG. 10B shows a variant shape of cylindrical rod 110b in which a central bore can be added to increase the vacuum power at the front of the rod. FIG. 10C shows a rod 110c whose profile is in the form a cross. FIG. 10D shows a rod whose profile is polygonal. Other shapes of rod can be imagined without departing from the scope of the description herein insofar as the suction forces exerted on the graft blocked by the rod inside the needle are homogeneous and symmetrical.

FIG. 10E is a perspective view showing a second mode of rapid attachment of an implantation needle to the piston 17 according to another embodiment of the description herein in which a hollow cylindrical needle 213 has at its posterior part a means of cylindrical or crown-shaped fastener 202 having two opposed longitudinal grooves 203 suitable for fitting by axial interlocking or snap-fastening in two claws 201 with elastic deformation and of the same dimension arranged at the cylindrical end 200 of the extension 171 of the piston 17. The grooves 203 once introduced and fixed in the claws 201 allow the locking in axial rotation of the needle 213 relative to the piston 17 so as to position the bevelled end of said needle in the same plane facing the skin surface as described previously. Such a fastening device has the advantage of being able to quickly remove the needle from the piston during the operation by forced withdrawal and its replacement by a new needle forcefully reintroduced into the channel 173 of the piston.

Other Embodiments

FIGS. 11 to 20 illustrate a second embodiment of an implantation device according to the description herein characterized in that it further comprises a mechanical means as a push button actuated by the finger of the operator, allowing controlled axial rotation of the implantation needle when the latter is in the action position ready to aspirate a graft. Indeed, medical practice has shown that it is easier to quickly aspirate a graft, already lined up or placed for example on the back of the hand or on a gauze, in the needle when the bevel of the needle is oriented facing the operator.

Once the graft is loaded into the needle, thanks to such a device, the operator can reposition more easily and more quickly the bevel of the needle facing the skin without having to perform a wrist rotation movement which can be a source of muscle fatigue taking into account the repetitiveness of the operating procedure as it will be described below.

Figures 11, 12, 13, 14, 15:
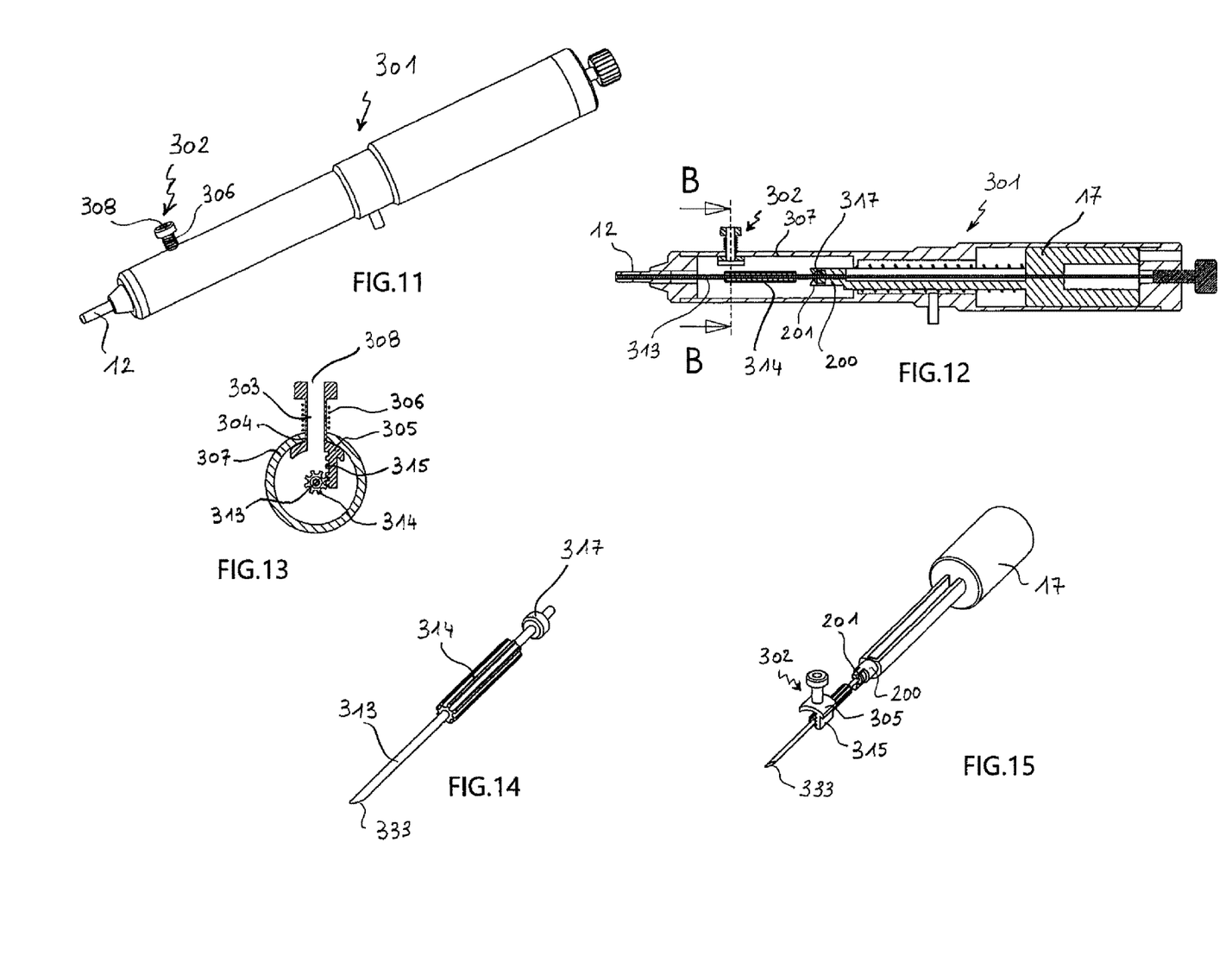
FIG. 11 is a perspective view showing a second embodiment of a device according to the description herein at rest position including a push button for the purpose of needle axial rotation.
FIG. 12 is a longitudinal sectional view of the instrument of FIG. 11.
FIG. 13 is an enlarged cross-sectional view B-B of FIG. 12 showing the mechanical relation between the push button and the needle.
FIG. 14 is a perspective view of a needle adapted to the instrument of FIG. 12.
FIG. 15 is a perspective view showing the mechanical relation between the push button and the needle fixed to the piston of FIG. 12.

FIGS. 11 to 13 are views of a graft implantation device 301 according to the description herein in a rest position in which an implantation needle is in the retracted position into the sheath 12 located at the front of the instrument.

In these FIGS., it can be seen that the graft implantation device 301 has all the mechanical and functional characteristics of the implantation device 1 described above with the addition of a push button 302 disposed at the anterior part of the instrument in place of the orifice 8 as described in FIG. 1. The push button 302 is composed of two parts, respectively external and internal relative to the implantation instrument 301. The external part is of cylindrical tubular shape, with type of hollow piston 303 pierced right through by an air exhaust port 308 communicating the outside air with the air contained inside the instrument 301. The hollow piston 303 is configured to move hermetically between two high and low positions in a cylindrical hole 304 made in the wall 307 of the implantation device 301.

The internal part of the push button has an enlargement or flange 305 of square and curved shape suitable for coming to adapt to the internal curvature of the wall 307. The flange 305 has a lateral extension of the rack type 315 suitable for coming to adapt and mesh perpendicularly in an axial gear or pinion 314 of a hollow needle 313 arranged in the axis of the piston 17. The hollow cylindrical needle 313 has at its rear part a quick coupling means of cylindrical shape or crown 317 adapted to come to fit by fitting together with a slight clearance at the end 200 of the piston 17, to which it is held by two elastic claws 201. Such a fastening means allows the needle 313 to be able to move in translation with the piston 17 within the implantation device 301 while retaining the possibility of free rotation about its axis relative to the piston 17. The orifice 308 of the push button is intended to be blocked by the index finger of the operator (not shown) in order to mobilize the needle 313 in front of the instrument as it has been described previously and will be described in more detail later.

In FIGS. 14 and 15 it can be seen that the needle 313 of hollow cylindrical shape with a bevelled anterior end 333 has at its middle part a crenellated part or pinion 314 extending over a distance suitable for meshing and remaining in contact with the rack 315 of the push button 302 when the needle is mobilized in axial translation with respect to said push button. The needle 313 has at its posterior part a crown 317 suitable for fitting by interlocking with a slight clearance to the end 200 of the piston 17, to which it is held by two elastic claws 201.

Such a positioning configuration of the needle 313 relative to the rack 315 makes it possible to easily orient the bevel 333 facing a right-handed operator (not shown) in a predefined initial starting plane relative to the position of the instrument held in the operator's right hand and especially with respect to the axis of the push button 302.

FIGS. 16 to 20 are views of the graft implantation device 301 according to the description herein in an action position where the piston 17 is in the front position within the instrument as well as the needle 313 protruding outside of the sheath 12.

Figures 16, 17, 18:
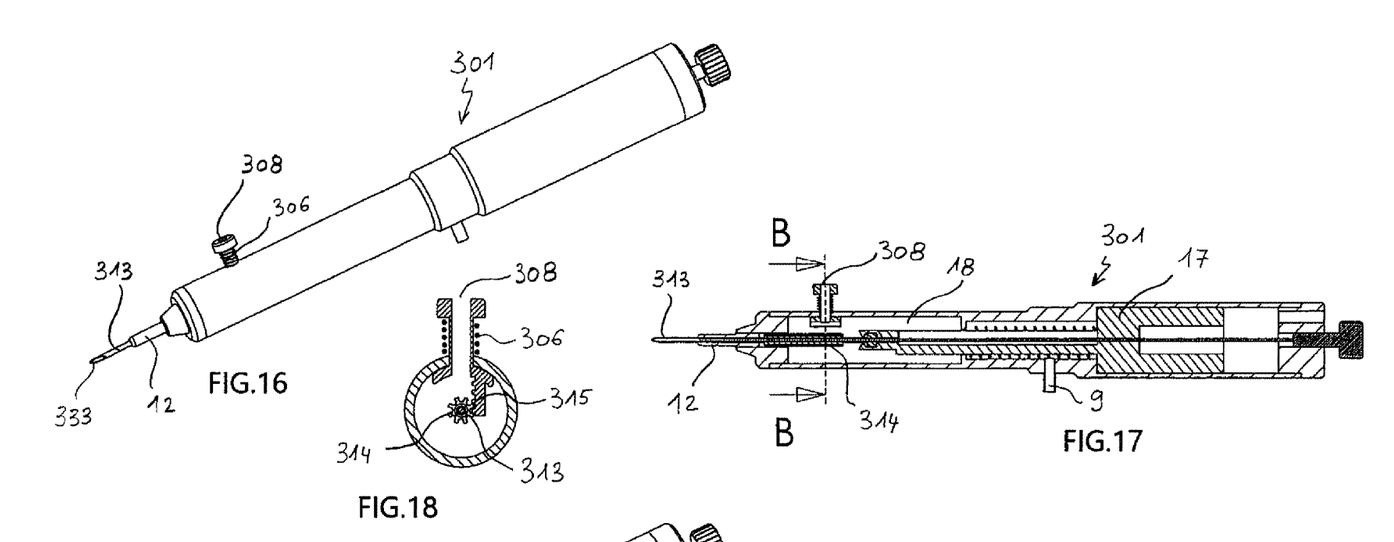
FIG. 16 is a perspective view of the device of FIG. 11 in action with the needle extending at the front part of the instrument in a position for graft loading in the needle by aspiration.
FIG. 17 is a longitudinal sectional view of the instrument of FIG. 16.
FIG. 18 is an enlarged cross-sectional view B-B of FIG. 17.

FIGS. 16, 17 and 18 illustrate the first step of this action position. The instrument 301 being connected to a vacuum source (not shown) by its channel 9, the obstruction of the orifice 308 by the operator's index finger (not shown) will cause a sudden depression inside the chamber 18 causing within the instrument the almost instantaneous forward displacement of the piston 17 and consequently the forward displacement of the needle 313 relative to the sheath 12 over an equivalent distance (for example approximately 10 millimeters). In this intermediate action position, the needle 313 still remains locked in rotation by the rack 315 located in the upper position engaged in the pinion 314 of the needle 313 so that the bevel 333 is still oriented towards the operator. Still in this position, the bevel 333 being in suction mode is then placed more easily in contact with a graft (not shown) disposed for example on the back of the left hand of the operator who is immediately sucked inside the needle 313.

Figures 19, 20, 21:
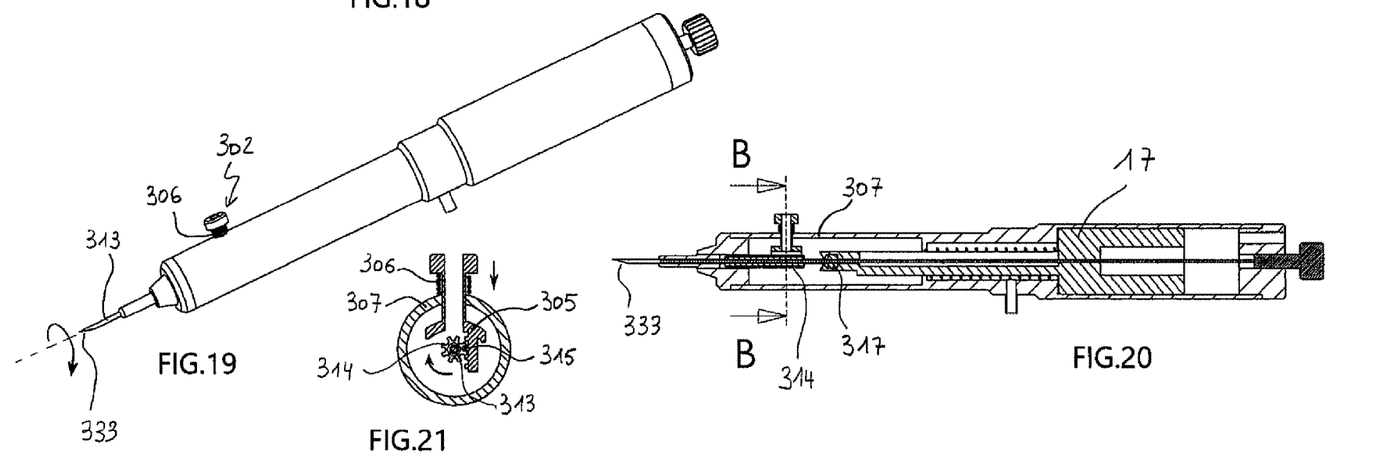
FIG. 19 is a perspective view of the device of FIG. 11 in action with the needle extending at the front part of the instrument in a position for graft insertion into the skin.
FIG. 20 is a longitudinal sectional view of the instrument of FIG. 19.
FIG. 21 is an enlarged cross-sectional view B-B of FIG. 20.

FIGS. 19, 20 and 21 illustrate the second step of the action position during which a stronger pressure of the operator's finger on the push button 302 will cause its displacement, for example by 2 millimeters, at the interior of the instrument and consequently the displacement of the rack 315 in the lower position as well as the axial rotation of the pinion 314 of the needle 313 so that the bevel 333 can be oriented immediately facing the skin. In this position, the needle is then introduced into the skin (not shown) and the release of the operator's finger on the push button 302 will cause the latter to return to the high position pushed by the spring 306 as well as the rapid withdrawal of the needle 313 inside the instrument by breaking the vacuum following the opening of the orifice 308, leaving in place the graft (not shown) perfectly positioned in the skin according to the same principle described above at FIG. 6B.

The instrument in the rest position is then ready to aspirate the next graft according to the same steps and the same principle and so on.

Such a graft implantation device comprising a mechanical means of controlled axial angular rotation of the needle not only allows a significant time saving but also a muscular relief of the operator's wrist, especially since it is a question of a repetitive act reproduced thousands of times in a single surgery session.

In FIGS. 11 to 20, the working principle of the graft implantation device 301 has been described for a right-handed operator with an angular rotation of the needle of a quarter of a turn at 90° clockwise rotation in order to present the bevel of the needle oriented first facing him and then downwards.

It is also conceivable to use the graft implantation device by a left-handed operator by reversing the position of the push button relative to the instrument so that the rack 315 can engage in the pinion 314 on the opposite side and allow the needle to rotate counterclockwise in order to present the bevel 333 first facing the operator and then down.

It is also possible to reduce or increase the degree of rotation of the needle by pressing the push button to a greater or lesser level to adapt the position of the bevel of the needle to the variable curvature of the recipient skin area of the head.

Figure 22:
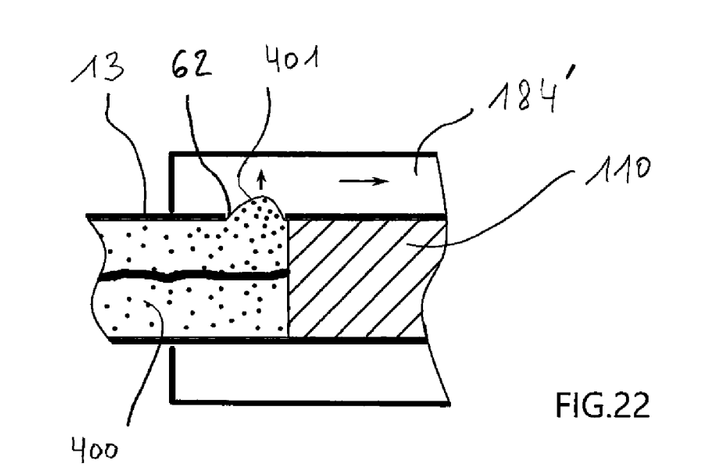
FIG. 22 is a partial detailed enlarged longitudinal sectional view of a loaded graft inside a needle in the anterior or prior art.

In FIG. 22, describing the prior art in the afore-mentioned U.S. Pat. No. 7,144,406, it can be seen that the graft 400 is sucked inside a needle 13 through a lateral orifice 62 located in the wall of the needle in communication with a suction space 184' connected to a vacuum source. The graft 400 remains blocked inside the needle by a rod 110. Such an arrangement has the drawback of causing the lateral suction of part of the graft 401 through the orifice 62 which can on the one hand traumatize the graft and on the other hand constitute a mechanical obstacle to the withdrawal of the needle 13 relative to rod 110.

Figure 23:
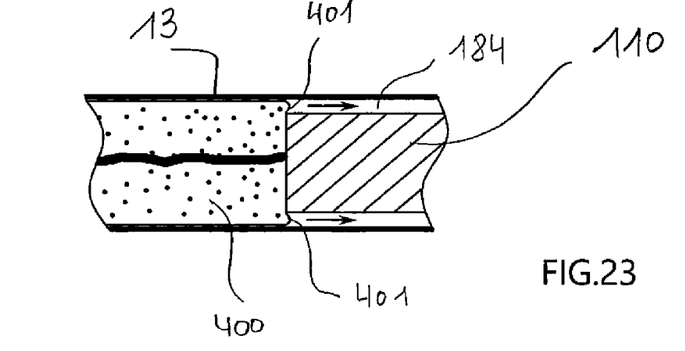
FIG. 23 is a partial detailed enlarged longitudinal sectional view of a loaded graft inside a needle of a device according to the description herein.

In FIG. 23, in contrast, it can be seen that according to the description herein, the graft 400 is sucked inside a needle 13 and remains blocked in contact with a rod 110 by means of a suction space 184 located between the rod 110 and the needle 13. If such an arrangement can cause a deformation 401 of the graft 400, this deformation is on the one hand negligible and is perfectly symmetrical in contact with the rod 110 and on the other hand it does not form a mechanical obstacle to withdrawal of the needle 13 relative to the rod 110.

Operation

FIG. 24A to 24F show the different detailed steps of loading a graft inside the needle and the graft placement into the skin of a device according to the description herein as described in FIGS. 1 to 8.

The device 1 according to the description herein is connected by a flexible tubing to a vacuum source for example a continuously operating electric pump of a sufficient vacuum power of 800 mBar. The instrument is held like a pen by the operator. At rest position the orifice 8 at the front part of the instrument is left opened and the implantation needle 13 staying in retracted position inside the sheath 12. Obstructing the orifice 8 by the index finger of the operator induces a sudden air vacuum inside the chamber 18 causing the instantaneous forward displacement of both piston 17 inside the instrument and needle 13 extending outside the tip 121 of sheath 12 at the front part of the instrument.

Figures 24A, 24B, 24C, 24D, 24E:
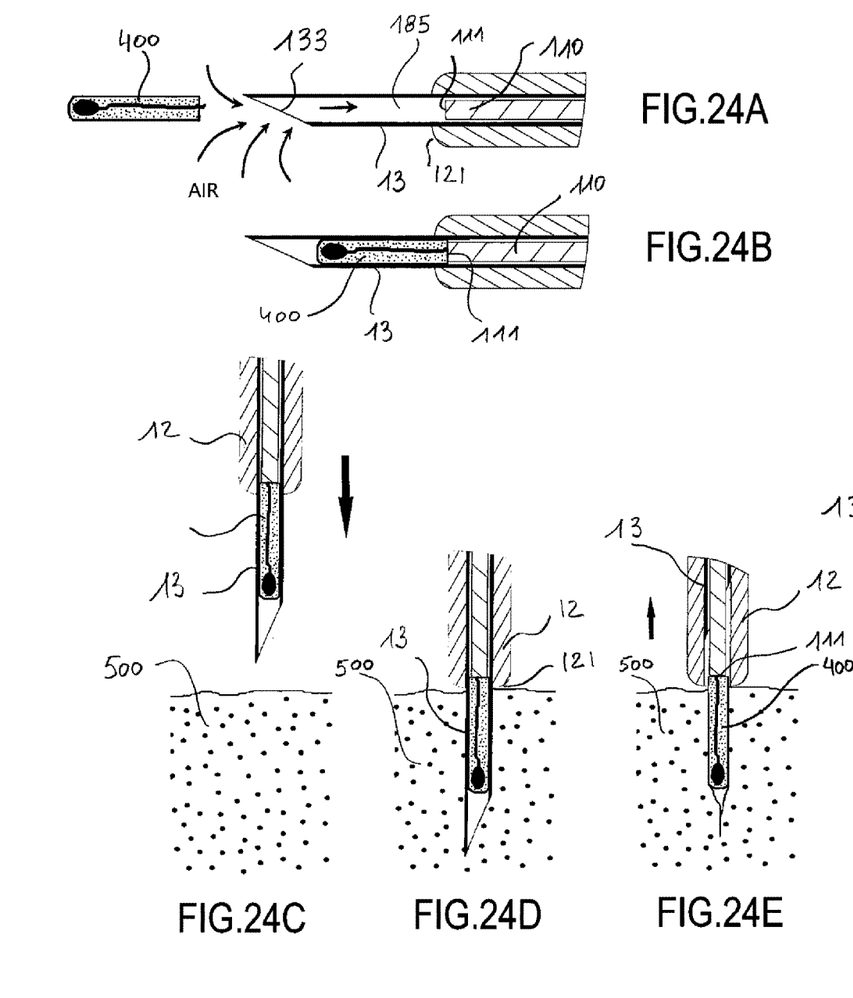
FIG. 24A to 24F are detailed sectional views showing the different steps of loading a graft inside the needle and placing the graft into the skin of a device according to the description herein as described in FIGS. 1 to 8.
Figure 24F:
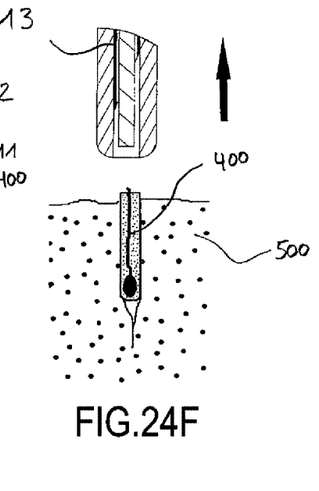

As shown in FIGS. 24A to 24B, the beveled open tip 133 of the needle becoming aspirative is brought in contact with the epidermal part of a previously harvested graft 400—lined up for example on the back of the left hand or on a moist gauze—thus having the effect of instantaneous loading completely the graft inside the space 185 of the needle 13. Since the orifice 8 is still kept blocked by the index finger, the instrument is moved to the recipient area of the skin 500 and the needle 13 is inserted totally into the skin until the tip 121 of the sheath 12 comes into contact with the skin surface, as shown in FIGS. 24C-24D. In that position, opening the orifice 8 by lifting the index finger breaks the vacuum inside the instrument causing the simultaneous release of the graft 400 from the needle 13 and the instantaneous retraction of the needle 13 inside the sheath 12 thanks to the backward displacement of the piston 17 at rest position, thus leaving the graft 400 perfectly positioned into the skin still maintained retained by the tip of the rod 111 as shown in FIG. 24E. The instrument is then removed from the skin surface as shown in FIG. 24F ready to pick up and place the next graft in the same manner and so on.

It is easily understood among the advantages of such a device according to the description herein, that it becomes possible with a little practice to implant directly into the skin more than two thousands grafts of excellent quality in less than an hour.

The embodiments illustrated and discussed in this specification are intended only to teach those skilled in the art how to make and use the disclosure herein. In describing embodiments of the disclosure herein, specific terminology is employed for the sake of clarity. However, the disclosure herein is not intended to be limited to the specific terminology so selected. The above-described embodiments of the disclosure herein may be modified or varied, without departing from the disclosure herein, as appreciated by those skilled in the art in light of the above teachings. It is therefore to be understood that, within the scope of the claims and their equivalents, the disclosure herein may be practiced otherwise than as specifically described.

The invention claimed is:

1. A device for implantation of hair grafts, comprising:
a handpiece extending along a longitudinal axis, wherein the handpiece has a sheath mounted to a forward end thereof and a channel to which a source of vacuum is connectable;
a piston slidably mounted in the handpiece and movable between a rest position and an action position, wherein the piston is biased to the rest position, wherein in the rest position the piston defines a chamber in the handpiece and forward of the piston, and wherein the handpiece has an orifice that vents the chamber to an outside of the handpiece;
a hollow needle fixed to a forward end of the piston and extending into the sheath; and
a central rod fixed to the handpiece and extending into the hollow needle, wherein a cross-section of the rod is configured with a space with respect to the needle to communicate a vacuum in the chamber to an interior of the needle.

2. The device according to claim 1, wherein the aspirated graft is inserted by the needle into a scalp incision while the orifice is closed and the piston extends the needle forwardly beyond the sheath, and wherein subsequent to insertion of the graft the orifice is opened causing the piston and the needle to retract to the rest position while the rod retains the graft implanted at its insertion position in the incision.

3. The device according to claim 2, wherein the needle comprises a sharp bevel-shaped tip configured to form the incision into a scalp for implantation of the hair graft.

4. The device according to claim 3, wherein the needle is mounted for rotational motion with respect to the handpiece so as to allow rotation of the bevel with respect to the orifice.

5. The device according to claim 1, wherein the central rod is adjustably fixed to the handpiece along the longitudinal direction thereof so as to adjust an implantation depth of the hair graft.

6. The device according to claim 1, wherein the central rod has a circular cross-section and wherein vacuum in the chamber is communicated to the interior of the needle via an annular gap around the circumference of the central rod.

7. The device according to claim 1, wherein the central rod has a cross-section comprised of at least one of cross-sections that are cruciform, polygonal, star-shaped and hollow.

8. The device according to claim 1, wherein in the rear position the hollow needle is sheathed by the sheath, and wherein closure of the orifice creates a vacuum in the chamber to move the piston to the action position where the piston extends the needle forwardly beyond the sheath such that the vacuum in the chamber is communicated via the cross-sectional shape of the rod to aspirate a hair graft into the needle.

9. The device according to claim 1, wherein closure of the orifice creates a vacuum in the chamber such that the vacuum in the chamber is communicated via the space in the cross-sectional shape of the rod to aspirate a hair graft into the needle.

10. A method for implantation of hair grafts, comprising aspiration of a hair graft directly into a hollow needle of an implantation device which includes central rod that extends into the hollow needle, wherein a cross-section of the rod is configured with a space with respect to the needle to communicate a vacuum to an interior of the needle so as to aspirate the hair graft directly into the needle via the vacuum.

* * * * *